US009643002B2

(12) United States Patent
Greenberg et al.

(10) Patent No.: US 9,643,002 B2
(45) Date of Patent: *May 9, 2017

(54) METHOD OF MANUFACTURING A FLEXIBLE CIRCUIT ELECTRODE ARRAY WITH AT LEAST ONE TACK OPENING

(75) Inventors: Robert J. Greenberg, Los Angeles, CA (US); Neil Hamilton Talbot, La Crescenta, CA (US); Jordan Matthew Neysmith, Pasadena, CA (US); James Singleton Little, Saugus, CA (US); Brian V. Mech, Stevenson Ranch, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/167,074

(22) Filed: Jun. 23, 2011

(65) Prior Publication Data
US 2011/0265322 A1     Nov. 3, 2011

Related U.S. Application Data

(60) Division of application No. 11/821,328, filed on Jun. 21, 2007, now Pat. No. 7,991,478, and a
(Continued)

(51) Int. Cl.
*A61N 1/05*     (2006.01)
*A61N 1/36*     (2006.01)
(Continued)

(52) U.S. Cl.
CPC ........ *A61N 1/0543* (2013.01); *A61N 1/36046* (2013.01); *H05K 1/118* (2013.01);
(Continued)

(58) Field of Classification Search
CPC ............ A61N 1/0543; Y10T 29/49117; Y10T 29/49156; Y10T 29/49158; H05K 3/0014
USPC ..... 29/825, 857, 858; 600/377, 378; 607/54, 607/118, 136, 137
See application file for complete search history.

(56) References Cited

U.S. PATENT DOCUMENTS 5,109,844 A      5/1992  de Juan, Jr. et al.
5,476,494 A  *  12/1995  Edell et al. ................... 607/116
(Continued)

FOREIGN PATENT DOCUMENTS

KR       2003035738 A  *  5/2003

OTHER PUBLICATIONS

Machine Translation of KR 2003035738 A, obtained Aug. 14, 2012.*
(Continued)

*Primary Examiner* — Livius R Cazan
(74) *Attorney, Agent, or Firm* — Scott B. Dunbar; Tomas Lendvai

(57) ABSTRACT

The present invention provides a flexible circuit electrode array adapted for neural stimulation, comprising: a polymer base layer; metal traces deposited on the polymer base layer, including electrodes suitable to stimulate neural tissue; a polymer top layer deposited on the polymer base layer and the metal traces at least one tack opening. The present invention provides further a method of making a flexible circuit electrode array comprising depositing a polymer base layer; depositing metal on the polymer base layer; patterning the metal to form metal traces; depositing a polymer top layer on the polymer base layer and the metal traces; and preparing at least one tack opening.

4 Claims, 12 Drawing Sheets

Related U.S. Application Data continuation-in-part of application No. 11/413,689, filed on Apr. 28, 2006, now Pat. No. 8,639,344, which is a continuation-in-part of application No. 11/207,644, filed on Aug. 19, 2005, now Pat. No. 8,014,878.

(60) Provisional application No. 60/815,311, filed on Jun. 21, 2006, provisional application No. 60/676,008, filed on Apr. 28, 2005.

(51) Int. Cl.
    *H05K 1/11*     (2006.01)
    *H05K 3/00*     (2006.01)

(52) U.S. Cl.
    CPC ....... *H05K 3/0014* (2013.01); *Y10T 29/49002* (2015.01); *Y10T 29/49117* (2015.01); *Y10T 29/49155* (2015.01); *Y10T 29/49174* (2015.01); *Y10T 29/49176* (2015.01)

(56) References Cited

U.S. PATENT DOCUMENTS

| | | | |
|---|---|---|---|
| 5,575,813 A | | 11/1996 | Edell et al. |
| 5,688,698 A | * | 11/1997 | Robinson et al. ............ 438/59 |
| 5,935,155 A | | 8/1999 | Humayun et al. |
| 5,944,747 A | | 8/1999 | Greenberg et al. |
| 6,374,143 B1 | | 4/2002 | Berrang et al. |
| 6,400,989 B1 | | 6/2002 | Eckmiller |
| 6,458,157 B1 | | 10/2002 | Suaning |
| 6,516,228 B1 | | 2/2003 | Berrang et al. |
| 6,843,870 B1 | | 1/2005 | Bluger |
| 2002/0091421 A1 | | 7/2002 | Greenberg et al. |
| 2002/0111658 A1 | * | 8/2002 | Greenberg et al. ........... 607/116 |
| 2002/0198573 A1 | * | 12/2002 | Nisch et al. .................... 607/54 |
| 2006/0225274 A1 | * | 10/2006 | Greenberg et al. ............ 29/846 |

OTHER PUBLICATIONS

Machine Translation of KR2003-0035738, obtained Dec. 6, 2012.*
Rizzo et al., Development of a Silicone Retinal Implant_ Surgical Methods and Mechanical Design, Massachusetts Institue of Technology, site version as of Apr. 29, 1999, http://www.ai.mit.edu/projects/implant/poster1.html.*
Shamma-Donoghue, et al., Thin-Film Multielectrode Arrays for a Cochlear Prosthesis; IEEE Trans. Elec. Dev., vol. Ed-29, No. 1, Jan. 1982.

* cited by examiner

METHOD OF MANUFACTURING A FLEXIBLE CIRCUIT ELECTRODE ARRAY WITH AT LEAST ONE TACK OPENING

CROSS-REFERENCE TO RELATED APPLICATIONS

This application is a divisional of application Ser. No. 11/821,328, entitled "Flexible Circuit Electrode Array with at Least One Tack Opening", filed Jun. 21, 2007 and issued as U.S. Pat. No. 7,991,478, which claims the benefit of U.S. Provisional Application No. 60/815,311, "Flexible Circuit Electrode Array with at least one Tack Opening", filed Jun. 21, 2006 and which is a Continuation-In-Part of U.S. application Ser. No. 11/413,689 and issued as U.S. Pat. No. 8,639,344, "Flexible Circuit Electrode Array", filed Apr. 28, 2006, which is a Continuation-In-Part of U.S. application Ser. No. 11/207,644 and issued as U.S. Pat. No. 8,014,878, filed Aug. 19, 2005 which claims the benefit of U.S. Provisional Application No. 60/676,008, "Thin Film Electrode Array", filed Apr. 28, 2005, the disclosures of all are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for neural stimulation.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating or casting. A layer of metal, preferably platinum, is applied to the polymer and patterned to create electrodes and leads for those electrodes. Patterning is commonly done by photolithographic methods. A second layer of polymer is applied over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

The pressure applied against the retina, or other neural tissue, by an electrode array is critical. Too little pressure causes increased electrical resistance between the array and retina, along with electric field dispersion. Too much pressure may block blood flow causing retinal ischemia and hemorrhage. Pressure on the neural retina may also block axonal flow or cause neuronal atrophy leading to optic atrophy. Common flexible circuit fabrication techniques such as photolithography generally require that a flexible circuit electrode array be made flat. Since the retina is spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

It is further advantageous to provide a fold or twist in the flexible circuit array at the point where it passes through the sclera. Additional material may be added inside and outside the fold to promote a good seal with the scleral tissue.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
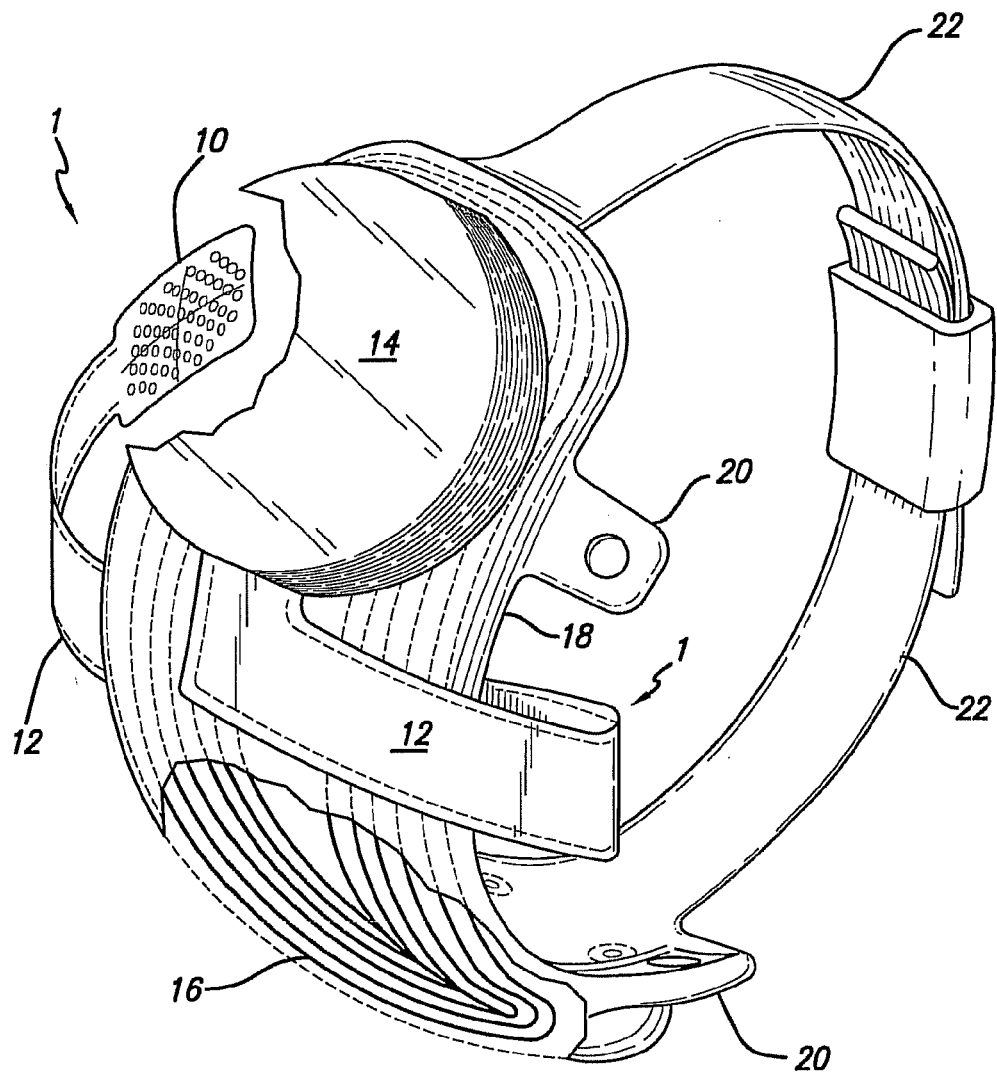
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
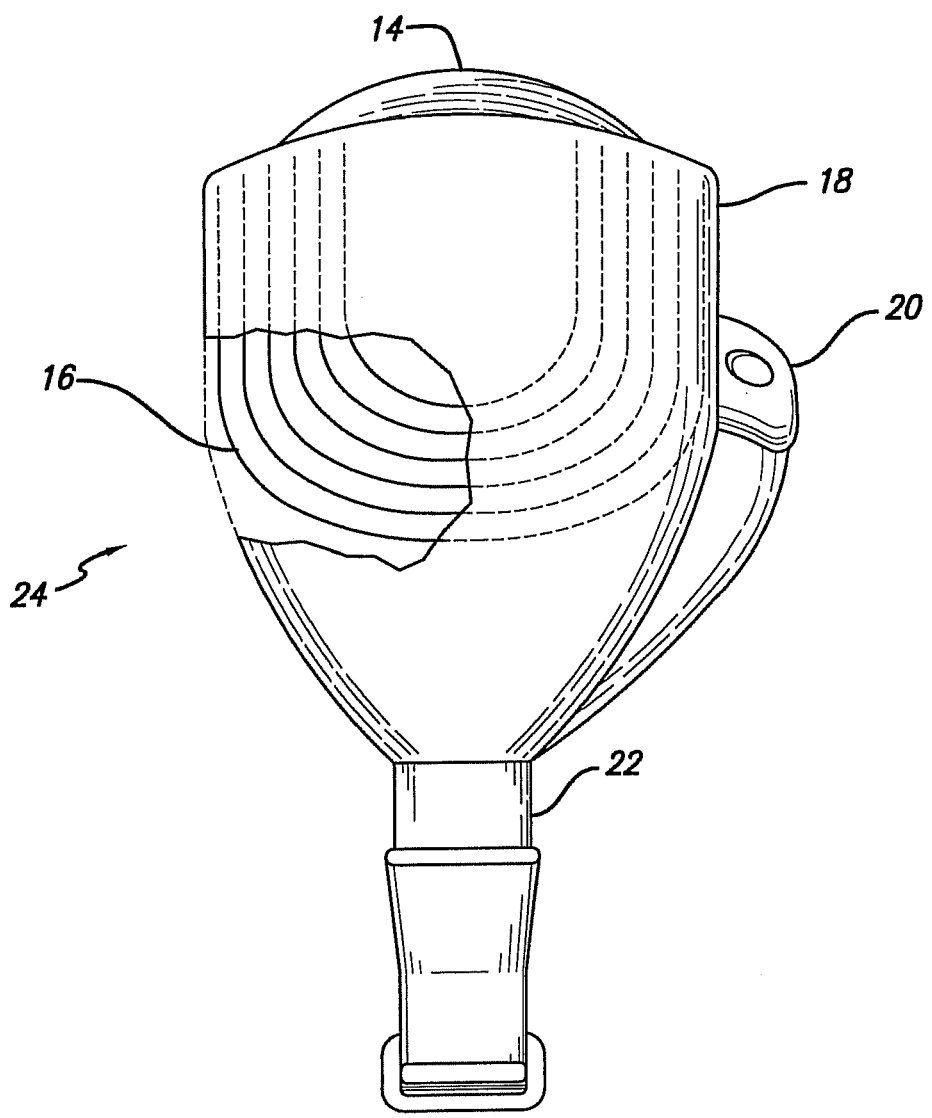
FIG. 2 is a side view of the implanted portion of the preferred retinal prosthesis showing the fan tail in more detail.
Figure 3A:
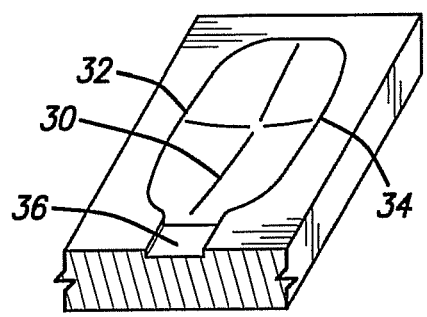
FIG. 3A-3E depict molds for forming the flexible circuit array in a curve.
Figure 3B:
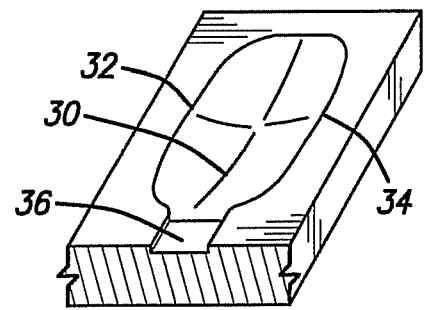
Figure 3C:
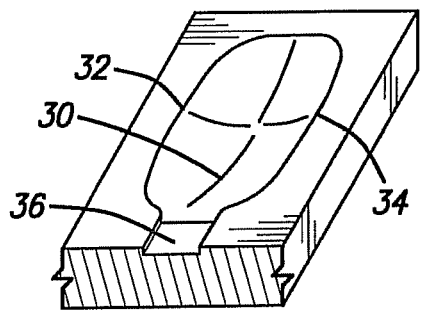
Figure 3D:
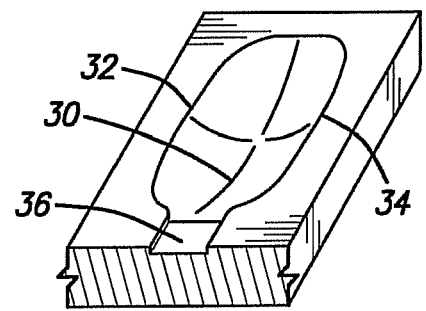
Figure 3E:
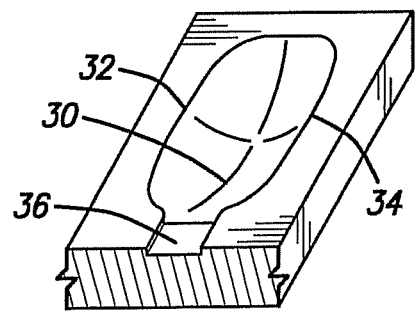

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode and bond pad to improve electrical continuity. This can be accomplished through any of the above methods or electroplating. Then, the top layer of polymer is applied over the metal. Openings in the top layer for electrical contact to the electronics package 14 and the electrodes may be accomplished by laser ablation or reactive ion etching (RIE) or photolithograph and wet etch. Making the electrode openings in the top layer smaller than the electrodes promotes adhesion by avoiding delaminating around the electrode edges.

The pressure applied against the retina by the flexible circuit electrode array is critical. Too little pressure causes increased electrical resistance between the array and retina. It should be noted that while the present invention is described in terms of application to the retina, the techniques described are equally applicable to many forms of neural stimulation. Application to the retina requires a convex spherical curve. Application to the cochlea requires a constant curve in one dimension and a spiral curve in the other. Application to the cerebral cortex requires a concave spherical curve. Cortical stimulation is useful for artificial vision or hearing, touch and motor control for limb prostheses, deep brain stimulation for Parkinson's disease and multiple sclerosis, and many other applications.

Common flexible circuit fabrication techniques such as photolithography generally require that a flexible circuit electrode array be made flat. Since the retina is spherical, a flat array will necessarily apply more pressure near its edges, than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIGS. 3A-3E illustrate a series of molds according to the preferred embodiment. Since the flexible circuit will maintain a constant length, the curvature must be slowly increased along that length. As the curvature 30 decreases in successive molds (FIGS. 3A-3E) the straight line length between ends 32 and 34, must decrease to keep the length along the curvature 30 constant, where the mold in FIG. 3E approximates the curvature of the retina or other desired neural tissue. The molds provide a further opening 36 for the flexible circuit cable 12 of the array to exit the mold without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array and the retina. Hence, the amount of curvature is a compromise between the desired curvature, array surface area, and the properties of the material.

Figure 4:
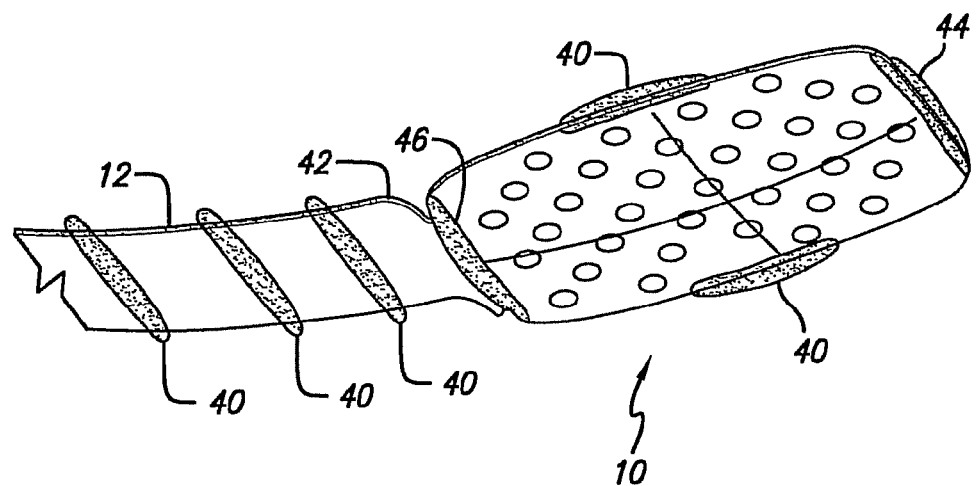
FIG. 4 depicts an alternate view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array to round the edges and protect the retina. Silicone around the entire edge may make the flexible circuit less flexible. So, it is advantageous to provide silicone bumpers or ribs to hold the edge of the flexible circuit electrode array away from the retinal tissue. Curvature 40 fits against the retina. The leading edge 44 is most likely to cause damage and is therefore fit with molded silicone bumper. Also, edge 46, where the array lifts off the retina can cause damage and should be fit with a bumper. Any space along the side edges of curvature 40 may cause damage and may be fit with bumpers as well. It is also possible for the flexible circuit cable 12 of the electrode array to contact the retina. It is, therefore, advantageous to add periodic bumpers along the flexible circuit cable 12.

It is also advantageous to create a reverse curve or service loop in the flexible circuit cable 12 of the flexible circuit electrode array to gently lift the flexible circuit cable 12 off the retina and curve it away from the retina, before it pierces the sclera at a sclerotomy. It is not necessary to heat curve the service loop as described above, the flexible circuit electrode array can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array must be inside the sclera in order to contact the retina. The sclera is cut through at the pars plana, forming a sclerotomy, and the flexible circuit passed through the sclerotomy. A flexible circuit is thin but wide. The more electrode wires, the wider the flexible circuit must be. It may be difficult to seal a sclerotomy over a flexible circuit wide enough to support enough wires for a high resolution array. A narrow sclerotomy is preferable.

Figure 5:
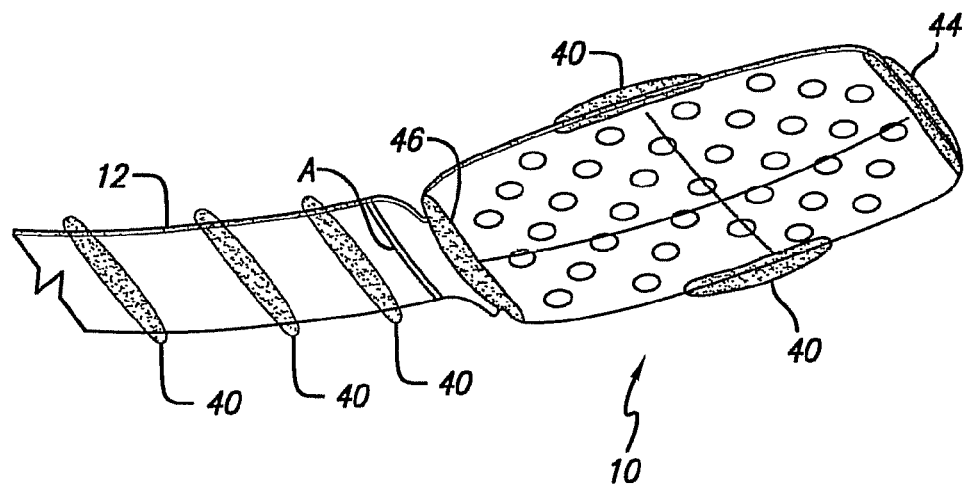
FIG. 5 depicts an alternative view of the invention with ribs to help maintain curvature and prevent retinal damage fold of the flexible circuit cable and a fold A between the circuit electrode array and the flexible circuit cable.

FIG. 5 depicts a further embodiment of the part of the prosthesis shown in FIG. 4 with a fold A between the circuit electrode array 10 and the flexible circuit cable 12. The angle in the fold A also called ankle has an angle of 1°-180°, preferably 80°-120°. The fold A is advantageous since it reduces tension and enables an effective attachment of the flexible electrode circuit array 10 to the retina.

Figure 6:
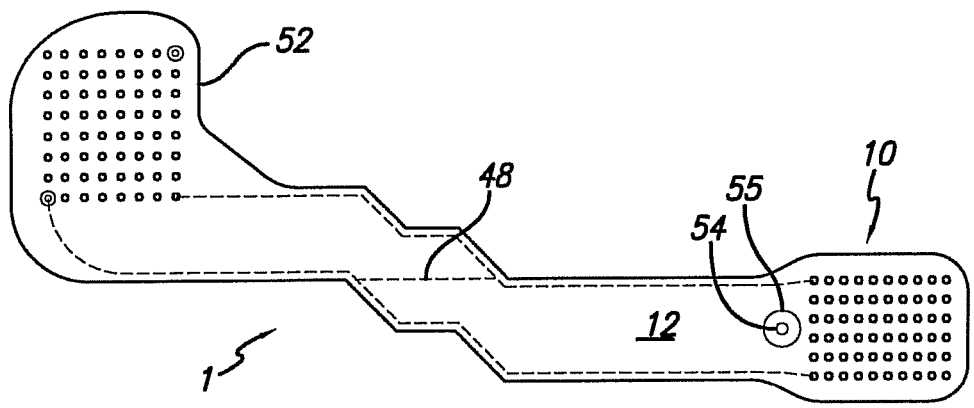
FIG. 6 depicts the flexible circuit array before it is folded and attached to the implanted portion.

FIG. 6 shows the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 7:
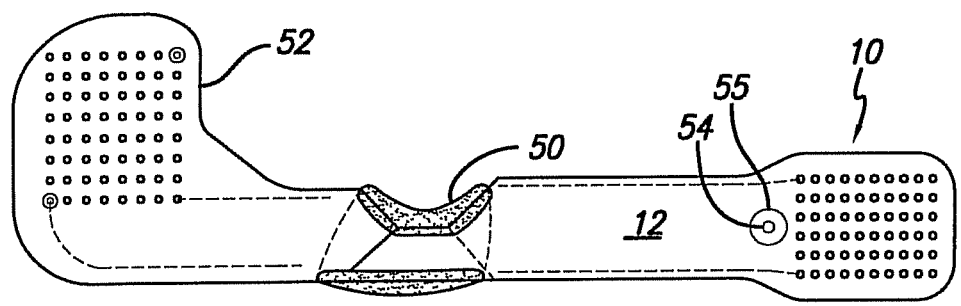
FIG. 7 depicts the flexible circuit array folded.

FIG. 7 shows the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture.

FIG. 7 shows that it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-Tex or similar material would bond with scleral tissue and promote healing. In particular, a porous material will allow scleral tissue to grow into the pores promoting a good bond.

Figure 8:
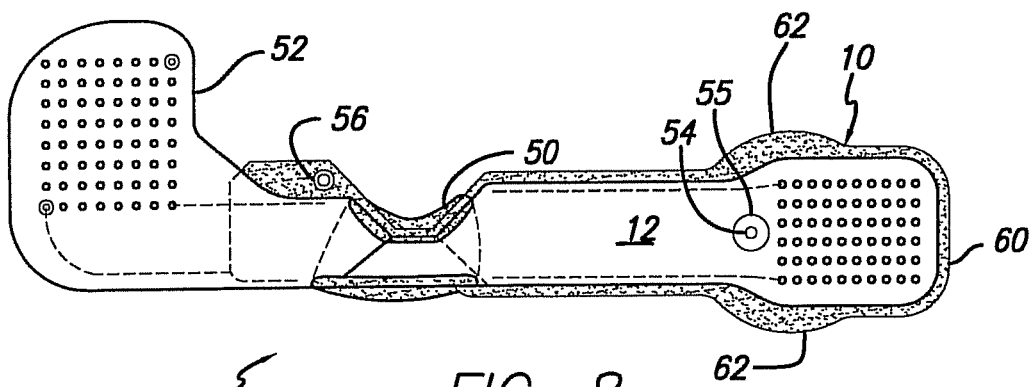
FIG. 8 depicts a flexible circuit array with a protective skirt.

FIG. 8 shows that the flexible circuit electrode array 10 may be inserted through the sclera, behind the retina and placed between the retina and choroid to stimulate the retina subretinally. In this case, it is advantageous to provide a widened portion, or stop, of the flexible circuit cable 12 to limit how far the flexible circuit electrode array is inserted and to limit the transmission of stress through the sclera. The stop may be widening of the flexible circuit 1 or it may be added material such as a bumper or sleeve.

A skirt 60 covers the flexible circuit electrode array 10, and extends beyond its edges. It is further advantageous to include wings 62 adjacent to the attachment point 54 to spread any stress of attachment over a larger area of the retina. There are several ways of forming and bonding the skirt 60. The skirt 60 may be directly bonded through surface activation or indirectly bonded using an adhesive.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue.

Figure 9:
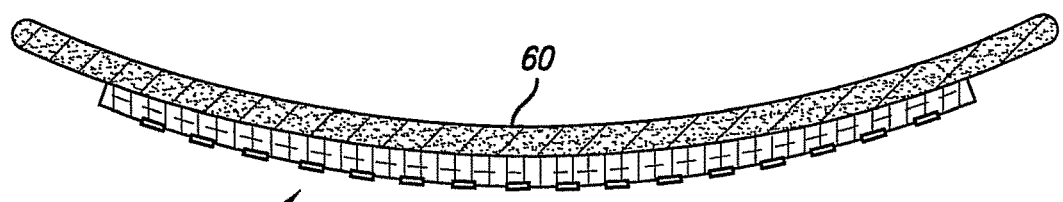
FIG. 9 depicts a flexible circuit array with a protective skirt bonded to the back side of the flexible circuit array.
Figure 10:
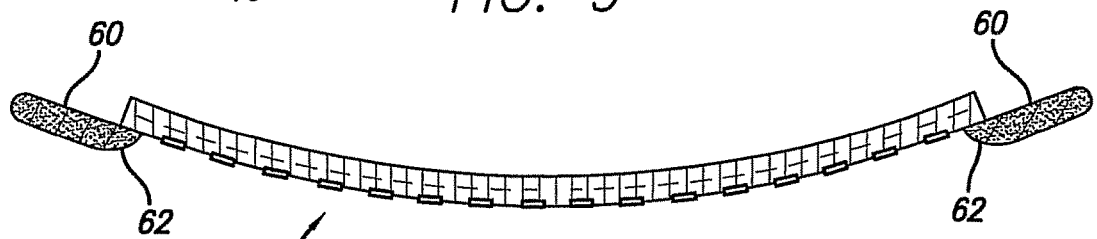
FIG. 10 depicts a flexible circuit array with a protective skirt bonded to the front side of the flexible circuit array.

The simplest solution is to bond the skirt 60 to the back side (away from the retina) of the flexible circuit electrode array 10 as shown in FIG. 9. While this is the simplest mechanical solution, sharp edges of the flexible circuit electrode array 10 may contact the delicate retina tissue. Bonding the skirt to the front side (toward the retina) of the flexible circuit electrode array 10 will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 11:
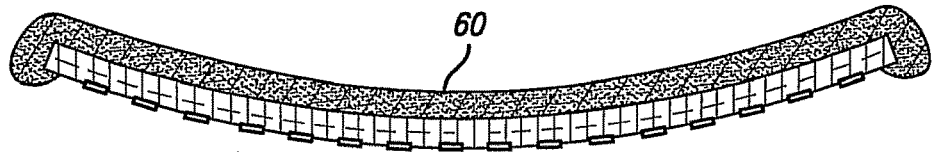
FIG. 11 depicts a flexible circuit array with a protective skirt bonded to the back side of the flexible circuit array and molded around the edges of the flexible circuit array.

FIG. 11 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 12:
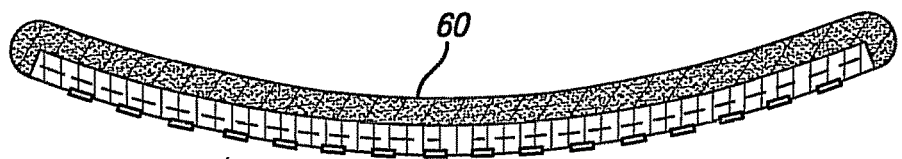
FIG. 12 depicts a flexible circuit array with a protective skirt bonded to the back side of the flexible circuit array and molded around the edges of the flexible circuit array and flush with the front side of the array.

FIG. 12 shows a flexible circuit electrode array 10 similar to FIG. 11, with the skirt 60, flush with the front side of the flexible circuit electrode array 10 rather than extending beyond the front side. While this is more difficult to manufacture, it does not lift the electrodes off the retinal surface as with the array in FIG. 8. It should be noted that FIGS. 9-12 show skirt 60 material along the back of the flexible circuit electrode array 10 that is not necessary other than for bonding purposes. If there is sufficient bond with the flexible circuit electrode array 10, it may advantageous to thin or remove portions of the skirt 60 material for weight reduction.

Figure 13:
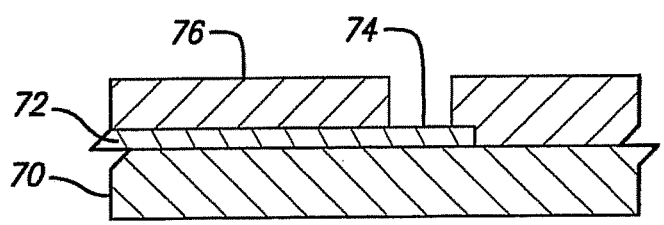
FIG. 13 is an enlarged view of a single electrode within the flexible circuit electrode array.

Referring to FIG. 13, the flexible circuit electrode array 10 is manufactured in layers. A base layer of polymer 70 is laid down, commonly by some form of chemical vapor deposition, spinning, meniscus coating or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 6-8). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 14:
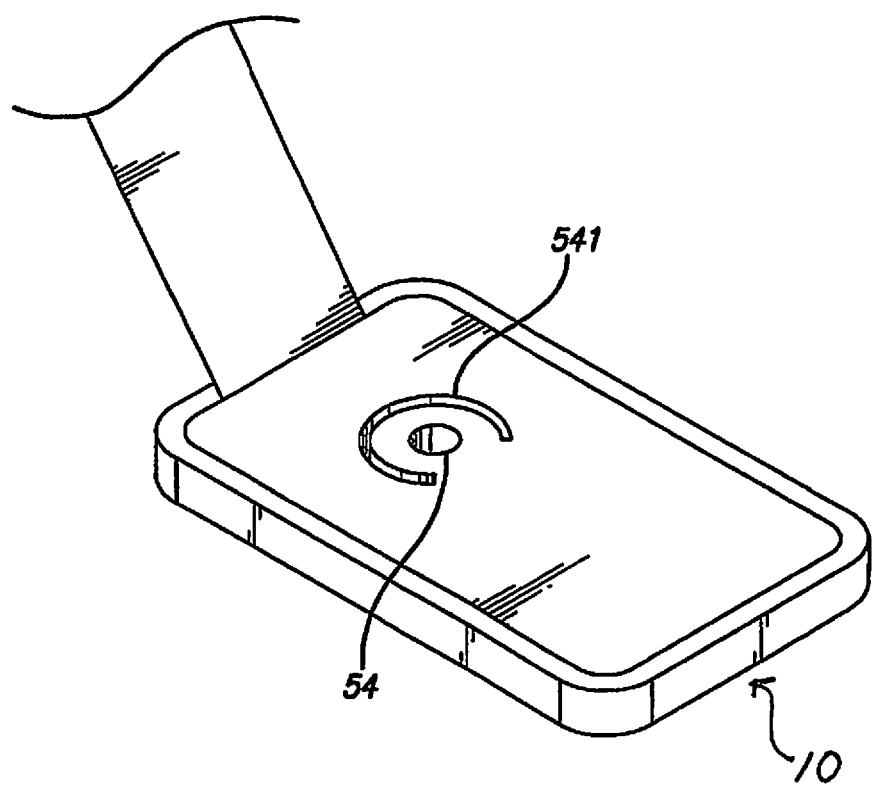
FIG. 14 shows a top view of a flexible electrode with a tack opening.

FIG. 14 shows a perspective view of a flexible electrode array 10 with a tack opening 54. The tack opening 54 is in the vicinity of defined, here c shape cut out 541. The cut out 541 decouples force from the tack opening 54 to portions of the flexible electrode array 10. The cutout 541 allows independent deflection of different regions. The cut out 541 as well as the opening 54 can be manufactured by different process, such as laser, assorted mechanical means, or molding process.

Figure 15:
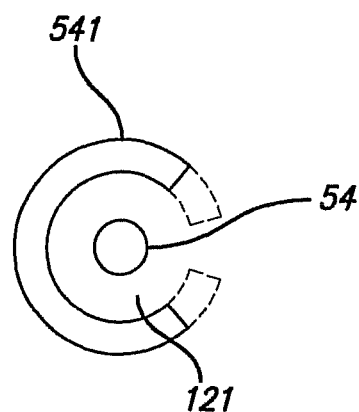
FIG. 15 shows a top view of a modified tack opening, which is made thinner and has an increased open angle.
Figure 16:
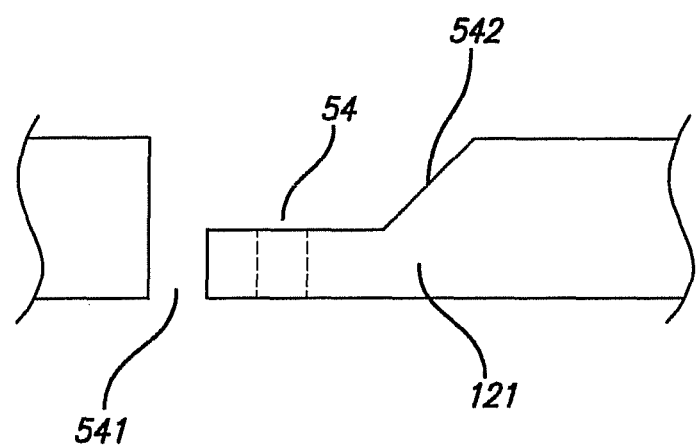
FIG. 16 shows a cross-sectional view of a modified tack opening, which is made thinner and has an increased open angle.

FIG. 15 shows a top view of a modified tack opening 54, which is made thinner and has an increased open angle 542. FIG. 16 shows a cross-sectional view of a modified tack opening, which is made thinner and has an increased open angle 542. FIGS. 15 and 16 further explain the modification shown in FIG. 14. By making the material 121 thinner between the tack hole 54 and the cut out 541 it becomes more flexible.

Figure 17:
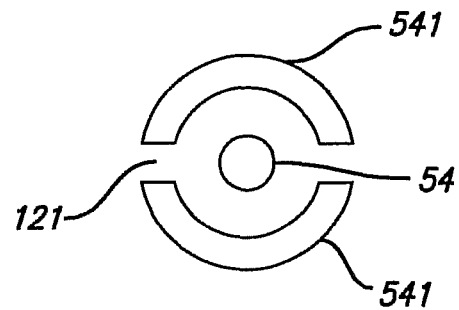
FIG. 17 shows a top view of a modified tack opening, which can be thin height, rotate better, adjust the angle better and use softer material.
Figure 18:
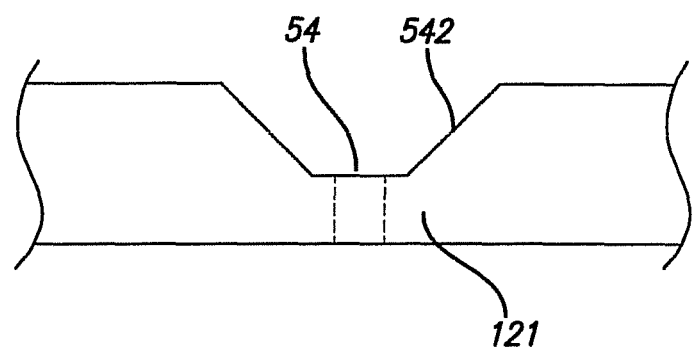
FIG. 18 shows a cross-sectional view of a modified tack opening, which can be thin height, rotate better, adjust the angle better and use softer material.

FIG. 17 shows a top view of a modified tack opening, which can be thin-height, rotate better, adjust the angle better and use softer material. FIG. 18 shows a cross-sectional view of a modified tack opening, which can be thin-height, rotate better, adjust the angle better and use softer material. FIG. 17 shows an alternative embodiment of the embodiment shown in FIG. 15. The c shaped cut outs may decouple the forces in a different way as discussed before for one c shaped cutout in FIG. 15.

Figure 19:
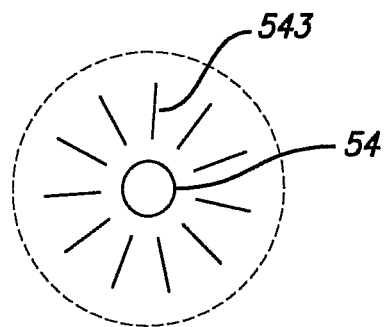
FIG. 19 shows a top view of a modified tack opening, which can adjust the diameter, and adjust thickness, can use softer materials, can be manufactured integrally or discretely, flush or protruding.

FIG. 19 shows a top view of a modified tack opening, which can adjust the diameter, and adjust thickness, can use softer materials, can be manufactured integrally or discretely, flush or protruding.

Figure 20A:
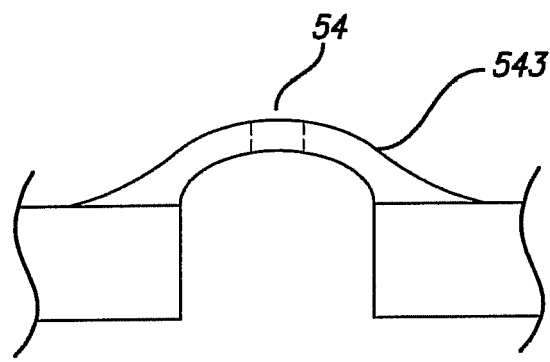
FIG. 20A and FIG. 20B show a cross-sectional view of a modified tack opening, which can adjust the diameter, and adjust thickness, which can use softer materials, and can be manufactured integrally or discretely, flush or protruding.
Figure 20B:
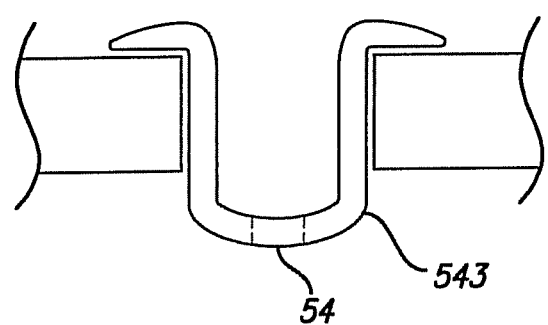

FIG. 20A and FIG. 20B show a cross-sectional view of a modified tack opening, which can adjust the diameter, and adjust thickness, can use softer materials, can be manufactured integrally or discretely, flush or protruding. FIG. 19, FIGS. 20A and 20B show a membrane 543 made of a soft polymer, such as silicone or mixtures thereof with other soft polymers. The membrane 543 contains the tack opening 54. This embodiment does not require a gap 541 and presents a more continuous surface. The membrane 543 and the opening 54 can be located on the top or bottom to the tack opening.

Figure 21A:
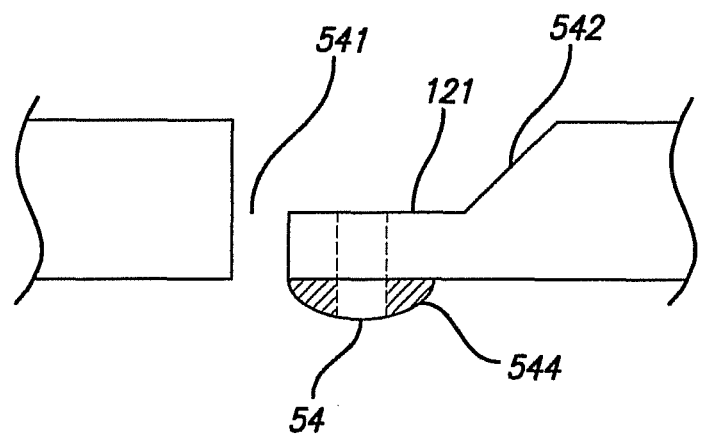
FIG. 21A and FIG. 21B show a cross-sectional view of a modified tack opening.
Figure 21B:
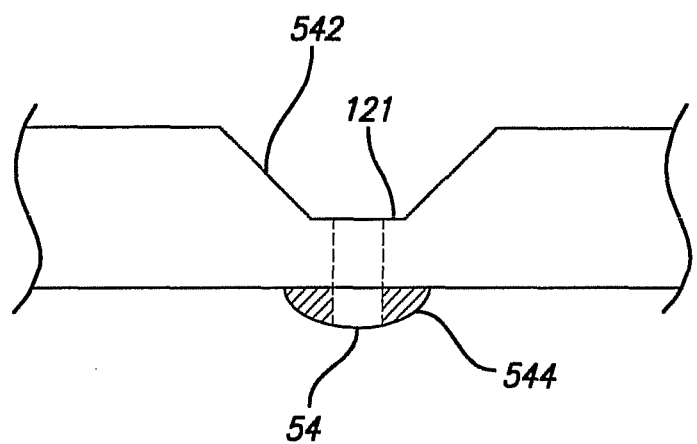

FIG. 21A and FIG. 21B show a cross-sectional view of a modified tack opening 54, which applies to the modifications in FIGS. 14-18, which can be flat (disk) or curved (hemispherical), and can be fabricated as part of the array or added separately. The figure shows in particular a pedestal 544 feature. The potential benefit lies in lifting global electrode region off retina by a small amount and localizing high pressure on tissue to tack site. FIG. 21A shows a shape cut out 541. FIG. 21B shows an open angle opening 542.

Figure 22:
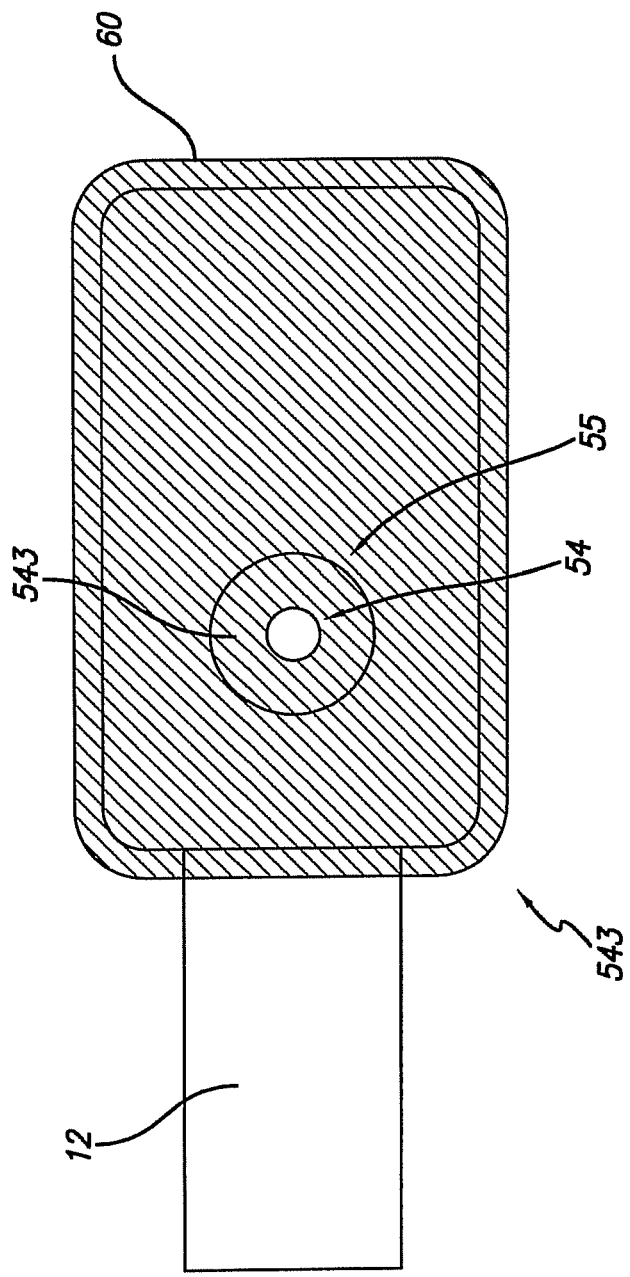
FIG. 22 shows a top view of a flexible electrode with a tack opening containing membrane material.
Figure 23:
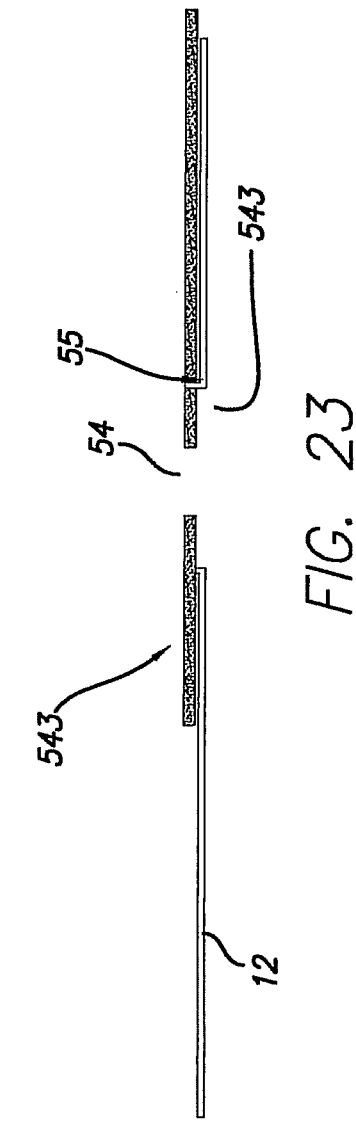
FIG. 23 shows a cross-sectional view of a flexible electrode with a tack opening containing membrane material.

FIG. 22 shows a top view and FIG. 23 shows a cross sectional view of a flexible electrode 12 with a tack opening 54 containing membrane material 543 and a silicone coating 60. FIG. 22 is similar to FIGS. 19, 20A and 20B except that this embodiment is more flat. It could be manufactured in faster and easier method as the previous variation. Due to the material properties of the membrane, small static forces are transferred to the electrode array to maintain contact proximity but large, transient forces are not transferred to reduce the likelihood of array and/or retinal damage.

Accordingly, what has been shown is an improved method of making a neural electrode array and improved method of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A method of making a flexible circuit electrode array comprising:

depositing a polymer base layer, hard enough to support metal traces;

depositing metal on said polymer base layer;

patterning said metal to form metal traces and metal electrodes;

depositing a polymer top layer on said polymer base layer and said metal traces preparing openings in said polymer top layer to expose said electrodes;

depositing a soft polymer layer, softer than said polymer base layer, over said polymer top layer including covering at least a portion of its edges, the soft polymer layer being a part of the final device and suitable to protect neural tissue from the flexible circuit;

preparing at least one first tack opening through said polymer base layer and said polymer top layer near said electrodes suitable for attaching said flexible circuit electrode array to a retina; and forming a membrane of polymer softer than said polymer base layer around the first tack opening, and forming a second tack opening within, and smaller than, said first tack opening, through the membrane of polymer, the softer polymer reducing stress transmitted from a tack to the flexible circuit electrode array.

2. The method according to claim 1, wherein said flexible circuit electrode array is made thinner around said tack opening forming said stress relief feature, as compared with material immediately surrounding said stress relief feature.

3. The method according to claim 1, wherein said stress relief feature is said tack opening surrounded by a flat or hemisphere shaped membrane.

4. The method according to claim 1, further comprising the step of molding a portion of said flexible circuit electrode array containing electrodes in an approximately convex spherical curve, to match the curvature of a retina.

* * * * *